(12) United States Patent
Dittmer et al.

(10) Patent No.: US 6,669,659 B2
(45) Date of Patent: Dec. 30, 2003

(54) PORTABLE FOLDABLE SPLINT

(76) Inventors: Andrew M. Dittmer, 913 Primrose Ave., Pell Lake, WI (US) 53157; Shelia D. Dittmer, 913 Primrose Ave., Pell Lake, WI (US) 53157

( * ) Notice: Subject to any disclaimer, the term of this patent is extended or adjusted under 35 U.S.C. 154(b) by 0 days.

(21) Appl. No.: 10/079,543

(22) Filed: Feb. 22, 2002

(65) Prior Publication Data

US 2003/0163070 A1 Aug. 28, 2003

(51) Int. Cl.$^7$ .................................................. A61F 5/00
(52) U.S. Cl. ........................ 602/5; 602/23; 602/26; 602/16
(58) Field of Search ................ 602/5, 23, 26, 602/6, 16; 482/148

(56) References Cited

U.S. PATENT DOCUMENTS

| | | | |
|---|---|---|---|
| 1,295,297 A | | 2/1919 | French |
| 1,559,339 A | | 10/1925 | Masland |
| 2,558,986 A | | 7/1951 | Seelert |
| 2,834,341 A | * | 5/1958 | Stryker |
| 3,099,448 A | | 7/1963 | Salvo et al. |
| 4,340,041 A | | 7/1982 | Frank |
| 4,485,808 A | | 12/1984 | Hepburn |
| 4,492,225 A | * | 1/1985 | Picolet et al. |
| 4,573,455 A | | 3/1986 | Hoy |
| 4,580,555 A | * | 4/1986 | Coppess |
| 4,643,176 A | | 2/1987 | Mason et al. |
| 4,708,131 A | | 11/1987 | Kendrick |
| 4,726,362 A | | 2/1988 | Nelson |
| 4,771,768 A | | 9/1988 | Crispin |
| 4,960,115 A | * | 10/1990 | Ranciato |
| RE33,621 E | | 6/1991 | Lamb et al. |
| 5,101,815 A | | 4/1992 | Langdon-Orr et al. |
| 5,232,435 A | | 8/1993 | Leibinsohn |
| 5,336,160 A | | 8/1994 | Christensen |
| 5,382,223 A | * | 1/1995 | Springs |
| 5,460,599 A | | 10/1995 | Davis et al. |
| 5,618,263 A | * | 4/1997 | Alivizatos |
| 5,800,371 A | * | 9/1998 | Winn |
| 5,865,695 A | | 2/1999 | Mahala et al. |
| 5,891,066 A | * | 4/1999 | Borschneck et al. |
| 5,954,676 A | * | 9/1999 | Kramer, III |
| 6,179,798 B1 | | 1/2001 | Nelson |

* cited by examiner

*Primary Examiner*—Nicholas D. Lucchesi
*Assistant Examiner*—Lalita M Hamilton
(74) *Attorney, Agent, or Firm*—David A. Tamburro

(57) ABSTRACT

A foldable, lightweight adjustable splint comprises a plurality of segments, with each segment having first and second ends and front and rear faces. Each segment has cooperating retaining structure at the first and second ends which permit the first end of one segment to be connected to the second end of an adjacent segment so that an endless number of segments may be connected together and folded into side-by-side relationship with respect to each other. Cooperating locking elements at the first and second ends permit the first end of one segment to be angularly adjusted with respect to the second end of an adjacent segment and then locked in a desired adjusted position. A plurality of straps fasten the segments to a part of a body.

20 Claims, 3 Drawing Sheets

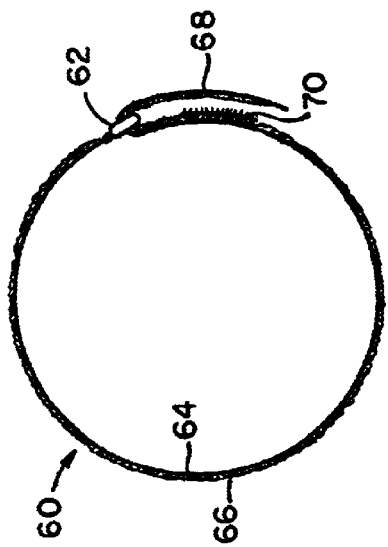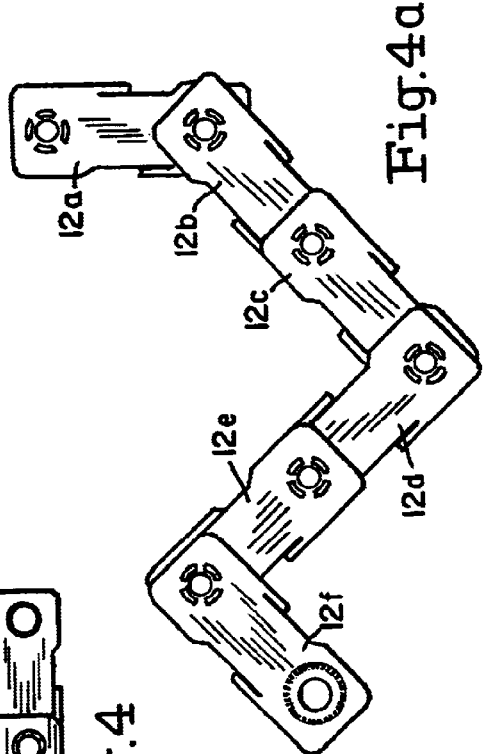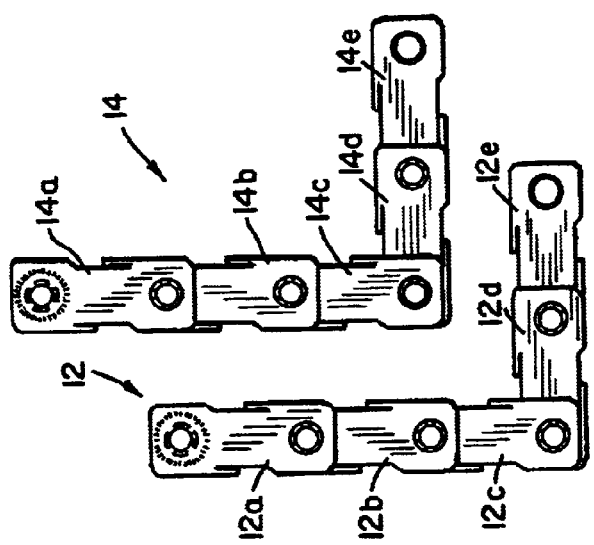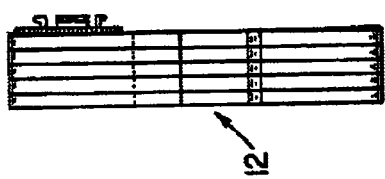

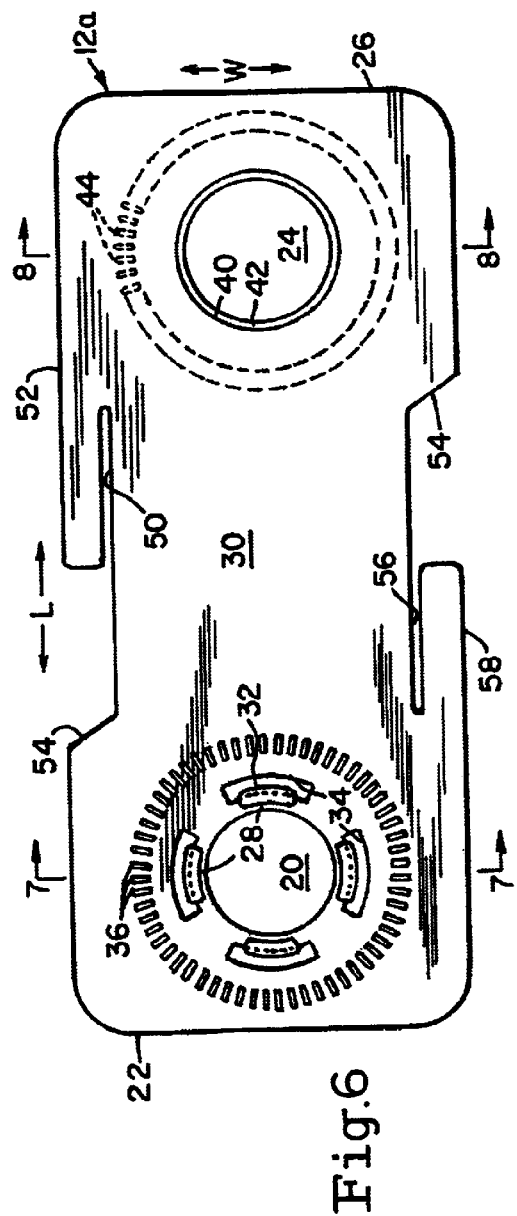
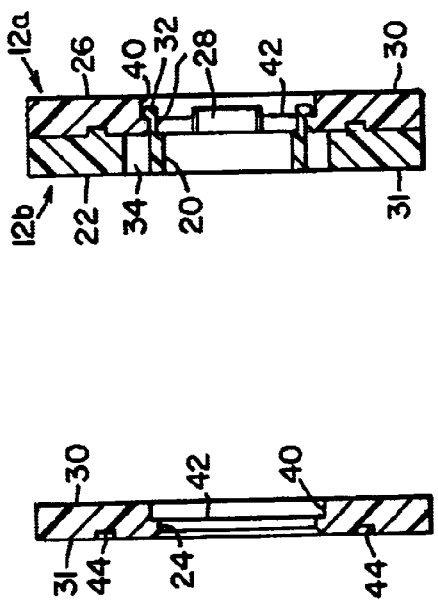
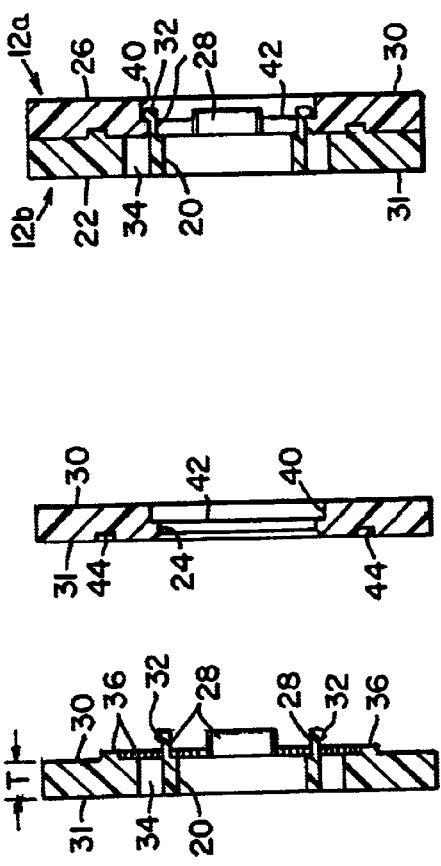

PORTABLE FOLDABLE SPLINT

BACKGROUND OF THE INVENTION

This invention relates generally to a medical splint and more particularly to a portable foldable lightweight splint which is especially useful by outdoorsmen, campers, athletes, etc.

Medical splints have been widely available but most of them have been cumbersome and awkward to carry and store and are difficult for individuals to apply in emergency conditions. Outdoorsmen such as campers and hikers often must carry their food and equipment with them and thus are constantly confronted with minimizing the size and weight of that equipment.

One piece of medical equipment which outdoorsmen consider necessary to take with them is a medical splint for use in an emergency to restrain movement of a body part such as an arm, wrist, leg or ankle following an accident or fall. Preferably the splint should be lightweight, small in size and easy to carry, expandable to accommodate placement around an arm or leg but must also be strong enough to restrain and support the arm or leg until the outdoorsmen can receive attention in a proper medical facility.

The medical splint of the invention as described hereinafter, has been developed to satisfy those needs.

SUMMARY OF THE INVENTION

Accordingly, the primary object of this invention resides in the provision of a portable, foldable, medical splint which is light in weight and easy to store and carry.

Another object of the invention resides in the provision of the above-identified splint which includes a plurality of segments foldable upon themselves into a storage position but yet expandable and adjustable to provide a splint of desired length and configuration to accommodate and support a particular part of the human body such as an arm or leg.

Still another object of the invention resides in the provision of the above identified splint wherein an endless number of segments may be connected together to provide a splint of desired length.

Still another object of the invention resides in the provision of the above-identified splint wherein adjacent segments are rotatably connected together by a cooperating releasable lock mechanism which permits those adjacent segments to be folded back upon each other or to be angularly adjusted with respect to each other as required for application against the injured body part.

A further object of the invention is to provide the above-mentioned splint which comprises two adjustable side assemblies each including a plurality of segments adjustable with respect to each other, with the two assemblies being applied against opposite sides of an injured body part. Each of the segments includes a pair of slots through which a Velcro strap can slide so as to extend around the injured body part.

Another object of the invention is provide the above-mentioned splint wherein the segments have sufficient strength and stability so as to provide firm support for the injured body part when the side assemblies are firmly held in place by the Velcro straps.

Still another object of the invention resides in the provision of the above medical splint wherein the segments are constructed of a material such as polycarbon or ABS plastic and wherein no metal is contained in either the segments or the strap so that the splint may remain in place on the injured body part while X-rays are being taken.

Other objects and advantages will become readily apparent from reading the following detailed description of the invention wherein reference is made to the accompanying drawings.

BRIEF DESCRIPTION OF THE DRAWINGS

FIG. 3 is a side view of the folded splint taken along line 3—3 of FIG. 2;

FIG. 4 is a plan view of the splint of the invention with the various segments in extended adjustable positions;

FIG. 4a is another plan view of the splint with the segments in various angular positions;

FIG. 5 is a schematic perspective view of the strap which is used with each of the segments of the foldable splint of the invention;

FIG. 6 is a top plan view of one of the segments forming the splint, the segment being illustrated in essentially full size;

FIG. 7 is a fragmentary sectional view taken along line 7—7 of FIG. 6;

FIG. 8 is a fragmentary sectional view taken along line 8—8 of FIG. 6;

FIG. 9 is a fragmentary sectional view taken along line 9—9 of FIGS. 1 and 4a illustrating the releasable, rotatable locking mechanism by which one end of a segment is locked together with the adjacent end of a next segment.

DETAILED DESCRIPTION OF THE INVENTION

Figure 1:
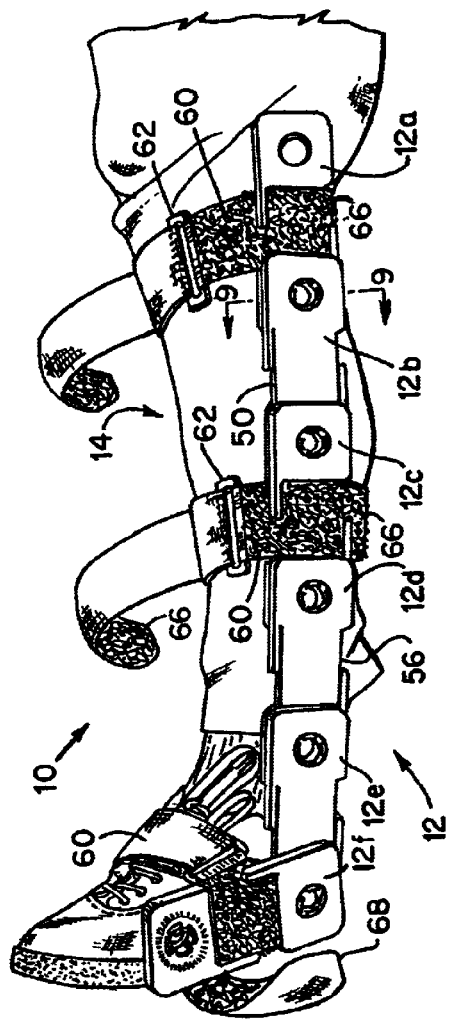
FIG. 1 is a generally perspective view of the foldable, adjustable splint of the invention as applied to the injured leg of a person.

Referring now to the drawings, the novel splint 10 of the invention includes a pair of adjustable side assemblies 12 and 14, with assembly 12 including a plurality of strips or segments 12a through 12e and assembly 14 including segments 14a through 14e. All the segments 12a through 12e and 14a through 14e are identical in construction and are shown in FIGS. 6–9.

The construction of each of the segments is illustrated in FIGS. 6–8 in essentially full size and will be described with respect to segment 12a. Each segment is of generally rectangular shape and has a width W of about 2 ½ inches, a length L of about 6 inches and a thickness T of about ³⁄₁₆ inches.

An opening 20 is provided at the left end 22 of the segment and a larger opening 24 is provided at the right end 26 of the segment. Openings 20 and 24 are centered along the width W of the segment and are spaced a center distance of about 4 inches along the length L of the segment. As shown in FIGS. 6 and 7 a plurality of locking projections or fingers 28 project outwardly from the front face 30 of the segment, with each finger 28 including an outwardly radially projecting lug 32. A clear opening 34 is provided radially outwardly of each of the fingers 28.

Also projecting outwardly from front face 30 are a plurality of equally radially spaced elements or teeth 36 on a radius outwardly beyond lugs 32 and openings 34.

At the other end 26 of the segment a counter bore 40 extends inwardly from front face 30 to opening 24 and provides an annular locking shoulder 42. A plurality of equally spaced shallow elements or recesses 44 equal in number to teeth 36 are formed in the rear face 31 of the segment and extend around opening 24 so as to align with teeth 36 when one end 22 of one of the segments is locked together with one end 26 of a next adjacent segment. The way in which these adjacent ends lock together is illustrated in FIG. 9. For example, when the end 26 of segment 12a is placed over the end 22 of segment 12b, fingers 28 and lugs 32 are snapped in place through opening 24 to the position illustrated in FIG. 9 so that the lugs 32 engage and lock against annular shoulder 42 and teeth 36 align with and nest within recesses 44.

The end 26 of segment 12a can thus be releasably rotatably locked in any adjusted position with the end 22 of segment 12b and retained in that position by the locking engagement between teeth 36 and recesses 44 and lugs 32 engaging against shoulder 43. The fingers 28 and lugs 32 have some flexibility which enable the two segments to be rotatably adjusted with respect to each other to obtain any desired adjusted position but the fingers and lugs are sufficiently rigid to hold the segments in that desired position once it is obtained.

Figure 2:
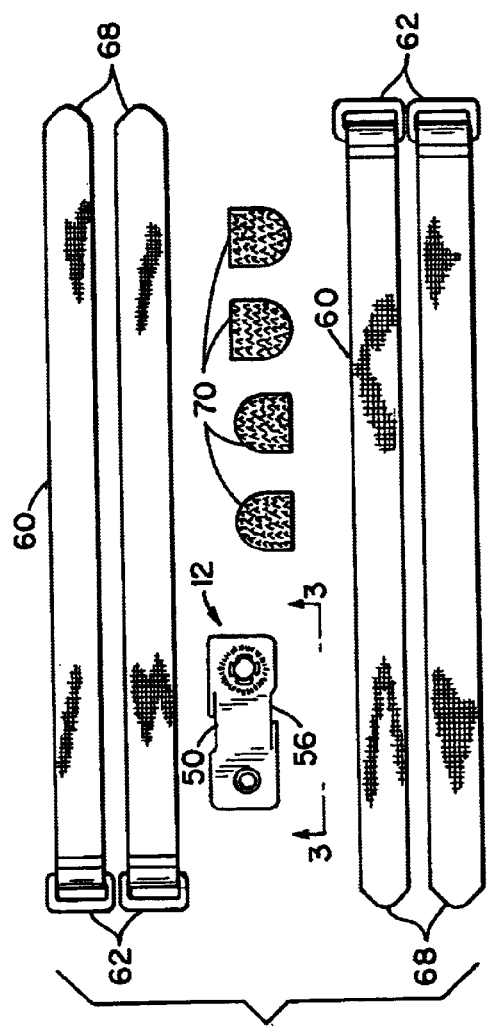
FIG. 2 is a top plan view of the splint of the invention in its folded condition, together with the Velcro straps and pads for holding the splint on the leg.

Each splint assembly 12 and 14 include any number of segments, for example 4–7 segments in each assembly, with each assembly being quickly put together by simply snapping the fingers 28 on one end of a segment through the opening 24 on the other end of an adjacent segment as illustrated in FIG. 9. When the splint is not in use, each of the assemblies can be quickly folded in a storage position illustrated in FIGS. 2 and 3 simply by rotating adjacent segments back upon themselves so that they overly each other in a folded, compact arrangement as illustrated in those drawings.

As illustrated in FIG. 1, when the splint assemblies 12 and 14 are placed on opposite sides of a body part such as the injured leg of a person, a Velcro strap 60 wraps around opposing segments of assemblies 12 and 14 and the leg of the person to hold the splint firmly in place. As shown in FIG. 6, each segment includes an upper slot 50 extending along the length of the segment and positioned adjacent the upper edge 52 of the segment, with the slot 50 including an open access portion 54 which breaks through that upper edge so that a strap 60 may be slid through portion 54 down into slot 50. Similarly a slot 56 is provided adjacent the lower edge 58 and includes an access portion 59 for receiving the strap.

As illustrated in FIG. 5, each strap 60 has a buckle 62 at one end, a smooth finished inner side 64 and a rough outer side formed by Velcro surface 66, with the free end 68 passing through the buckle 62 and bending back upon itself to lock against a double sided Velcro pad 70 which is removable from and reattachable to the outside surface 66 to accommodate a body part of any size.

In use when placing the splint on an injured body part, for example the leg or ankle as shown in FIG. 1, the segments of each assembly 12 and 14 are adjusted to a desired position and then placed on opposite sides of the leg and ankle. The free end of a strap 60 is then placed outwardly through slot 50 on segment 12c around the outside of the segment inwardly through slot 56, extended around the bottom of the leg, placed outwardly through slot 56 of segment 14c upwardly over the outside of the segment and inwardly through slot 50 of segment 14c, over the top of the leg through buckle 62 and folded back upon itself into tight locking engagement with the Velcro pad 70. A strap 60 is then similarly applied to the remaining opposing segments. When completed, because the straps pass through slots 50 and 56 of each segment, the straps firmly hold the assemblies 12 and 14 in place on the injured body part, with the smooth inside surface 64 of the straps wrapping around the body part and causing no irritation thereto. The two assemblies 12 and 14 of the splint 10 are held firmly in place and the splint has sufficient strength and stability to restrain movement of the body part and keep it immobile until the injured person can get to a proper medical facility.

It is apparent that the invention as described above accomplishes the objectives initially set forth and provides a medical splint which is foldable, compact, lightweight, but yet sufficiently stable and rigid when applied to a body part to keep that body part from moving. The splint is readily adjustable to accommodate various angular positions as necessary. It is quickly and easily applied and made commercially available at a reasonable cost.

The invention may be embodied in other specific forms without departing from the spirit or essential characteristics thereof the present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A foldable, adjustable splint comprising a plurality of segments, each segment having first and second ends and front and rear faces, cooperating retaining means at said first and second ends which permit the first end of one segment to be rotatably connected to the second end of an adjacent segment so that an endless number of segments may be connected together and folded with respect to each other with the front face of one segment lying in side-by-side relationship with the rear face of an adjacent segment, cooperating locking means at said first and second ends which permit the first end of one segment to be rotatably angularly adjusted with respect to the second end of an adjacent segment and then locked in a desired adjusted position, and means for fastening said segments to a part of a body.

2. The splint of claim 1, each segment including slot means, said fastening means being a strap which passes through said slot means.

3. The splint according to claim 2, each of said segments having upper and lower edges, said slot means including a first slot adjacent the upper edge and a second slot adjacent the lower edge, said strap passing through both of said slots.

4. The splint according to claim 3, each of said slots having a portion which breaks through its adjacent edge to facilitate placement of said strap in said slots.

5. A foldable, adjustable splint comprising a plurality of segments, each segment having first and second ends and front and rear faces, cooperating retaining means at said first and second ends which permit the first end of one segment to be connected to the second end of an adjacent segment so that an endless number of segments may be connected together and folded into side-by-side relationship with respect to each other, said retaining means including a plurality of fingers projecting outwardly from said front face at the first end of said segment and having radially extending retaining lugs, an opening through the segment at the second end thereof, a counterbore extending into said opening from said front face and providing an annular shoulder, the fingers at the first end of one segment passing through the opening at the second end of an adjacent segment to engage said lugs against said shoulder, cooperating locking means at said first and second ends which permit the first end of one segment to be angularly adjusted with respect to the second end of an adjacent segment and then locked in a desired adjusted position, and means for fastening said segments to a part of a body.

6. The splint according to claim 5, said cooperating locking means including a first plurality of angularly spaced elements on said front face extending around said fingers and a second plurality of angularly spaced elements on said rear face extending around said opening, said first and second elements engaging together to lock adjacent segments in a desired angular position.

7. The splint according to claim 6, each segment including slot means, said fastening means being a strap which passes through said slot means.

8. The splint according to claim 7, each of said segments having upper and lower edges, said slot means including a first slot adjacent the upper edge and a second slot adjacent the lower edge, said strap passing through both of said slots.

9. The splint according to claim 8, each of said slots having a portion which breaks through its adjacent edge to facilitate placement of said strap in said slots.

10. The splint according to claim 9, said strap having a buckle at one end, a smooth surface on one side and a rough surface on the other side, the free end of said strap being fed from the rear face of said segment through one of said slots over the front face of said segment inwardly through the other of said slots with the smooth surface positioned to engage around the body part and the leading end then being passed through the buckle and folded back upon itself to fasten the rough surfaces together.

11. A foldable adjustable splint comprising a pair of side assemblies, each assembly including a plurality of segments, each segment having first and second ends and front and rear faces, cooperating retaining means at said first and second ends which permit the first end of one segment to be rotatably connected to the second end of an adjacent segment so that an endless number of segments may be connected together and folded with respect to each other with the front face of one segment lying in side-by-side relationship with the rear face of an adjacent segment, cooperating locking means at said first and second ends which permit the first end of one segment to be rotatably angularly adjusted with respect to a second end of an adjacent segment and then locked in a desired adjusted position, and a plurality of straps for fastening said side assemblies on opposite sides of a part of a body.

12. The splint according to claim 11, each segment including slot means, one of said straps passing through said slot means in a segment of one of said side assemblies around said body part through said slot means in an opposite segment of said other side assembly and around said body part.

13. The splint according to claim 12, each of said segments having upper and lower edges, said slot means including a first slot adjacent said upper edge and a second slot adjacent the lower edge, said strap passing through both of said slots in opposing segments of said side assemblies and around said body part.

14. The splint according to claim 13, each of said slots having a portion which breaks through its adjacent edge to facilitate placement of said strap into said slots.

15. The splint according to claim 14, wherein each strap has a buckle at one end, a smooth inside surface, and an outer rough surface, the leading end of said strap passing through one of said slots from the rear face of one of said segments, over the front face inwardly through the second slot around said body part with the smooth face of said strap engaging said body part, the leading edge then similarly passing through the slots in an opposing segment of the other side assembly around the body part through the buckle, the leading edge of the strap then being folded back upon itself so that the rough surfaces are fastened together.

16. A foldable adjustable splint comprising a pair of side assemblies, each assembly including a plurality of segments, each segment having first and second ends and front and rear faces, cooperating retaining means at said first and second ends which permit the first end of one segment to be connected to the second end of an adjacent segment so that an endless number of segments may be connected together and folded into side-by-side relationship with respect to each other, said retaining means including a plurality of fingers projecting outwardly from said front face at the first end of said segment and having radially extending retaining lugs, an opening through the segment at the second end thereof, a counterbore extending into said opening from said front face and providing an annular shoulder, the fingers at the first end of one segment passing through the opening at the second end of an adjacent segment to engage said lugs against said shoulder, cooperating locking means at said first and second ends which permit the first end of one segment to be angularly adjusted with respect to a second end of an adjacent segment and then locked in a desired adjusted position, and a plurality of straps for fastening said side assemblies on opposite sides of a part of a body.

17. The splint according to claim 16, said cooperating locking means including a first plurality of angularly spaced elements on said front face extending around said fingers and a second plurality of angularly spaced elements on said rear face extending around said opening, said first and second elements engaging together to lock adjacent segments in a desired angular position.

18. The splint according to claim 17, each of said segments having upper and lower edges, a first slot adjacent said upper edge and an adjacent slot adjacent said lower edge, said strap passing through both of said slots and opposing segments of said side assemblies to fasten said side assemblies to the body part.

19. The splint according to claim 18, each of said slots having a portion which breaks through its adjacent edge to facilitate placement of said strap in said slots.

20. The splint according to claim 19, wherein each strap has a buckle at one end, a smooth inside surface, and an outer rough surface, the leading end of said strap passing through one of said slots from the rear face of one of said segments, over the front face inwardly through the second slot around said body part with the smooth face of said strap engaging said body part, the leading edge then similarly passing through the slots in an opposing segment of the other side assembly around the body part through the buckle, the leading edge of the strap then being folded back upon itself so that the rough surfaces are fastened together.

* * * * *